United States Patent [19]

Morelli et al.

[11] Patent Number: 5,709,857
[45] Date of Patent: Jan. 20, 1998

[54] LACTOBACILLUS STRAINS OF HUMAN ORIGIN, THEIR COMPOSITONS AND USES THEREOF

[75] Inventors: Lorenzo Morelli; Vittorio Bottazzi; Luigia Gozzini; Christoph De Haen, all of Milan, Italy

[73] Assignee: Dibra S.p.A., Italy

[21] Appl. No.: 664,447

[22] Filed: Jun. 17, 1996

Related U.S. Application Data

[63] Continuation of Ser. No. 448,840, May 24, 1995, abandoned.

[30] Foreign Application Priority Data

May 26, 1994 [IT] Italy .................................. MI94A1073
Aug. 25, 1994 [IT] Italy .................................. MI94A1773

[51] Int. Cl.[6] .............................. A01N 63/00; C12N 1/20
[52] U.S. Cl. ............................ 424/93.45; 435/252.9; 435/267; 426/61
[58] Field of Search ........................ 424/93.45; 426/61; 435/252.9, 822, 854, 267

[56] References Cited

U.S. PATENT DOCUMENTS

| 5,032,399 | 7/1991 | Gorbach et al. | 424/93 |
| 5,179,020 | 1/1993 | Herman et al. | 435/252.9 |

*Primary Examiner*—David M. Naff
*Assistant Examiner*—Deborah K. Ware
*Attorney, Agent, or Firm*—Nixon & Vanderhye

[57] ABSTRACT

The present invention concerns Lactobacillus strains and pharmaceutical compositions containing them.

7 Claims, No Drawings

LACTOBACILLUS STRAINS OF HUMAN ORIGIN, THEIR COMPOSITONS AND USES THEREOF

This is a Continuation of application Ser. No. 08/448, 840, filed May 24, 1995, now abandoned.

The present invention concerns Lactobacillus strains and pharmaceutical compositions containing them.

More in particular, the invention concerns the three new human Lactobacillus non-acidophilus strains characterized by the code number CNCM I-1390, CNCM I-1391 and CNCM I-1392, deposited at the CNCM Collection of the Institut Pasteur on Jan. 13, 1994, and a new human *Lactobacillus acidophilus* strain named CNCM I-1447 deposited at the same institute on Jul. 13, 1994 in accordance with the Treaty of Budapest.

The therapeutical use of lactic acid bacteria preparations has a long and well established tradition that dates back to the beginning of this century and to the studies that pointed out the beneficial effects of the use of fermented milk on the consumers' health conditions (Ref. 1–5).

Since then lactic acid bacteria have been widely used in the pharmaceutical industry and they constitute the active principle of various formulations for the treatment of intestinal diseases caused by pathogens, and as adjuvants in antibiotic treatments (Ref. 6–9).

During the past decades scientists deepened the knowledge on lactic acid bacteria in general, and on lactobacilli in particular, obtaining a remarkable amount of information.

However, the products presently on the market seem not to take into consideration the results of the most recent scientific studies (Ref. 10–11).

In particular, it should be pointed out that many studies have indicated that:

- lactobacilli play a peculiar role in the regulation of intestinal microflora, by producing both lactic acid and specific antibacterial substances (Ref. 12–16);
- these bacteria must come from the intestinal environment in which they will then be reimplanted (e.g., they must be isolated from the human intestinal system in order to be utilized for human beings, and so on) in order to guarantee the colonization considering the "host specificity" requirements (Ref. 17);
- lactobacilli are involved in several metabolic activities which are particularly relevant for the maintenance of the good conditions of health and for the prevention of several pathological conditions; in particular, nitrosamine degradation, bacterial toxin neutralization, and the anticancerogenic activity are worthy of mention (Ref. 18);
- the ability to adhere to the intestinal epithelium is an extremely advantageous feature for the intestinal bacteria (it is known that various pathogenic bacteria lose their virulence when they lose their ability to adhere to the mucosa); hence, the possibility of colonizing the epithelium can therefore be particularly important, for lactobacilli too, in order to provide a barrier to colonization of pathogenic bacteria (Ref. 10, 19);
- the taxonomic classification of the strains isolated from intestine has been deeply revised; the existence in this ecosystem of new bacterial species as well as the differentiation of specific biotypes within each species (Ref. 20) have been recognized;
- the "technological" properties of the strains (first of all the resistance to cryo-conservative treatments) are of particular importance in determining the possible exploitation of the lactic acid bacteria strains; in fact, the Lactobacillus strains so far used for probiotic purposes are generally slightly resistant to lyophilization conditions (Ref. 21). The adhesion properties must be maintained after lyophilization (requirement which is not always met).

In particular, in the attempt to isolate Lactobacillus strains endowed with high ability to adhere to the cells of the intestinal mucosa, isolation processes from "homologous" sources, such as the feces of healthy individuals, were described.

For example, U.S. Pat. No. 4,839,281, EP-A-199535 and U.S. Pat. No. 5,032,399 describe *Lactobacillus acidophilus* strains isolated from adults and characterized by strong adhesion properties, quantified as the number of bacterial cells that adhere to a cell of human intestinal mucosa, compared to a reference strain. However, the exact taxonomic classification of such a strain is doubtful, as the author himself, during the course of the substantive examination of the application by the American Patent Office, claimed that on the basis of the experimental data, the described Lactobacillus belonged to a non-acidophilus species (U.S. Pat. No. 4,839,281, File History, reply to the Office Action dated 30 Oct. 1987, page 7, last paragraph).

Reniero et al. (Ref. 27) reported the isolation of two strains of *Lactobacillus casei* from the feces of two infants. The presence in the feces of the same strains for several days led the author to attribute adhesion properties to these strains. No mention was made about other biological or technological properties like those mentioned above, which are distinct features of the Lactobacillus strains claimed in the present invention.

In fact, it was found that the CNCM I-1390, CNCM I-1391, CNCM I-1392 and CNCM I-1447 strains, beside adhesion to intestinal and buccal cells often superior to the reference strains, also had the following characteristic features:

- ability to inhibit the growth of human intestinal pathogens;
- ability to grow under a variety of conditions, both in aerobiosis and anaerobiosis, and at different pH values; these properties confer good capacity to adapt to the physiological and pathological situations that are met during the transit in the gastrointestinal tract;
- production of a large amount of lactic acid;
- high resistance to the bile;
- resistance to lyophilization, without losing adhesion ability.

These strains belong to the Lactobacillus genus and are characterized by a series of features that make them particularly interesting for the prophylaxis and treatment of several pathologies.

The invention provides pharmaceutical, veterinary or alimentary compositions comprising at least one of the CNCM I-1390, CNCM I-1391, CNCM I-1392 and CNCM I-1447 strains, preferably in a lyophilized form, mixed with an appropriate vehicle. These compositions can be administered orally or mixed with food products such as milk, yoghurt or milk-products, for the treatment or prophylaxis of gastrointestinal pathologies in which it is desirable to administer lactobacilli, as for example in the case of intestinal dismicrobism, diarrhoea of various origins, ulcerative colitis and related pathologies. The compositions of the present invention can also be administered in consequence of antibiotic treatments in order to preserve the non-pathological intestinal bacterial flora.

Another import ant feature of the strains of the present invention is that they were isolated from the feces of healthy newborns and weaned infants. In fact, it is known that the gastrointestinal tract of mammals is sterile at birth; it is rapidly colonized generally with the mother's vaginal and perianal flora. This natural route for the transfer of beneficial microorganisms is lacking in children born by caesarian delivery; as a matter of fact such children are more subjected to colonization by less favourable microorganisms. Colonization of the intestine by less favourable microorganisms has also been observed in premature infants. In both cases, this risk can be greatly reduced by oral administration of the strains of the present invention. Moreover, bottle-fed babies compared to breast-fed babies have an increased population of clostridia, coliforms and enterococci in their intestine. Also in this situation treatment with the lactobacilli of the present invention helps to reequilibrated the intestinal flora.

Said strains can also be formulated as mixtures of the strains of the present invention alone and/or together with other strains having complementary characteristics, i.e. different intrinsic properties. An example of such formulation can be represented by a mixture consisting of at least one strain endowed with strong adhesion properties in combination with at least one strain which produces high amounts of L-lactic acid. A preferred, but in no way limiting, composition can be prepared by mixing the strain of the present invention CNCM I-1394 and the strain *Enterococcus faecium* SF68 in suitable quantities, for instance from $10^6$ to $10^{10}$ cells of each strain, together with the usually employed additives or excipients.

Each single dose, typically in the form of capsules, solutions or drinkable suspensions, powder in sachets and similar forms, will generally contain from $10^6$ to $10^{10}$ cells of each strain.

The lactobacilli of the present invention have also been proved highly useful in improving the nutritional value of food products. Particularly preferred are dairy products obtained from milk and its derivatives.

Hereunder follows the isolation of the strains together with their characterization.

EXAMPLE 1

Isolation and Characterization of the Strains

The strains were isolated from newborns from the first day of life to the sixth. Samples were also taken from other infants during the weaning period.

Sampling was carried out on the subjects' feces taken twice a day in the clinic, and stored in sterile: swabs under anaerobic conditions. The selective primary isolation of the lactobacilli was carried out in a LBS™ selective medium (Lactobacillus Selection Agar, Oxoid). Plates were incubated under anaerobic conditions (Gas Pack system, BBL) for 48 h at 37° C. The colonies thus obtained were isolated in MRS liquid medium (de Man—Rogosa—Sharpe broth, Oxoid) and submitted to a first series of re-isolations in order: to obtain pure cultures (following smears on a selective agar medium, and isolation of single colonies). The se procedure s reflect the methodology proposed by Sharpe (Ref. 22). After isolation and purification, the strains were further characterized in order to select only those belonging to the Lactobacillus genus. The following characteristics were then examined: morphology (optical examination by phase-contrast microscope), reaction to Gram staining (positive for all the lactobacilli), the presence of catalase (negative for all the lactobacilli), and determination of the two lactic acid stereoisomers present in the culture medium of each strain after 24 h incubation (enzymatic determination by the Boehringer kit). As a result of these tests, it was possible to assign the isolates to the Lactobacillus genus. The strains were then lyophilized and stored at 4° C.

The analysis of the plasmid profiles, after alkaline extraction (Ref. 23), was then carried out on all the strains identified as lactobacilli. This analysis allowed the identification of the isolated strains (Ref. 24). The profile of soluble cytoplasmatic protein (Ref. 25) and pattern of the antibiotic resistances (Ref. 26) were also checked.

The representative strains of all the isolates were then analysed for their taxonomic allocation by means of standard phenotypic tests such as sugar fermentation pattern (API CH 50 galleries system, Biomerieux).

The taxonomy and the characteristics of the strains of the invention, are illustrated in the following charts:

| Chart 1 - Strain identification: CNCM I-1390 | | | | | |
|---|---|---|---|---|---|
| 1. | Origin: | human | | | |
| | Age: | weaned | Sex: | | F |
| | Type of delivery: | natural | Type of nutrition: | | breast-fed |
| 2. | Genus | Lactobacillus | | | |
| 3. | Morphology | Bacilli: | short | | |
| | | chains | yes | | |
| | | aggregates | no | | |
| | | presence of a capsule | no | | |
| 4. | Production of lactic acid | L<br>D | | 3.84 g/L<br>0.15 g/L | |
| 5. | Carbohydrate fermentation | | | | |
| | Glycerol | − | Erythrol | − | D-Arabinose − |
| | L-Arabinose | − | D-Xylose | − | L-Xylose − |
| | Adonitol | + | β-methyl- | − | Galactose + |
| | D-Glucose | + | xyloside | | D-Mannose + |
| | L-Sorbose | + | D-Fructose | + | Esculin + |
| | Salicin | + | Rhamnose | − | Maltose + |
| | Lactose | Variable | Cellobiose | + | Sucrose + |
| | Trealose | + | Melibiose | − | Melezitose + |
| | D-Raffinose | − | Inulin | + | Glycogen − |
| | Xylitol | − | Starch | − | Dulcitol − |
| | Inositol | − | β-Gentiobiose | − | Sorbitol − |
| | Amygdalin | − | Mannitol | + | D-Turanose + |
| | D-Lyxose | − | Arbutin | + | D-Fucose − |
| | D-Arabitol | − | D-Tagatose | + | Gluconate + |
| | α-methyl-D-mannoside | − | L-Arabitol | − | |
| | N-acetyl-glucosamine | + | α-methyl-D-glucoside<br>2-keto- | − | |
| | 5-keto-gluconate | − | gluconate<br>L-fucose | − | |
| | Ribose | + | | | |
| 6. | Plasmids: | two | | | |

| Chart 2 - Strain identification: CNCM I-1391 | | | | | |
|---|---|---|---|---|---|
| 1. | Origin: | human | | | |
| | Age: | weaned | Sex: | | F |
| | Type of delivery: | caesarian | Type of nutrition: | | bottle-fed |
| 2. | Genus | Lactobacillus | | | |
| 3. | Morphology | Bacilli: | short | | |
| | | chains | yes | | |
| | | aggregates | no | | |
| | | presence of a capsule | no | | |
| 4. | Production of lactic acid | L<br>D | | 3.14 g/L<br>0.20 g/L | |
| 5. | Carbohydrate fermentation | | | | |
| | Glycerol | − | Erythrol | − | D-Arabinose − |

Chart 2 - Strain identification: CNCM I-1391

| | | | | | | |
|---|---|---|---|---|---|---|
| L-Arabinose | − | D-Xylose | − | L-Xylose | − | |
| Adonitol | + | β-methyl- | | Galactose | + | |
| D-Glucose | + | xyloside | | D-Mannose | + | |
| L-Sorbose | + | D-Fructose | + | Esculin | + | |
| Salicin | + | Rhamnose | − | Maltose | + | |
| Lactose | + | Cellobiose | + | Sucrose | + | |
| Trealose | + | Melibiose | − | Melezitose | + | |
| D-Raffinose | − | Inulin | + | Glycogen | − | |
| Xylitol | − | Starch | − | Dulcitol | − | |
| Inositol | − | β-Gentiobiose | + | Sorbitol | − | |
| Amygdalin | + | Mannitol | + | D-Turanose | + | |
| D-Lyxose | − | Arbutin | + | D-Fucose | − | |
| D-Arabitol | − | D-Tagatose | + | Gluconate | + | |
| α-methyl-D-mannoside | − | L-Arabitol α-methyl-D-glucoside | − | | | |
| N-acetyl-glucosamine | + | 2-keto-gluconate | − | | | |
| 5-keto-gluconate | − | L-fucose | − | | | |
| Ribose | + | | | | | |
| 6. Plasmids: | five | | | | | |

Chart 3 - Strain identification: CNCM I-1392

| | | | | |
|---|---|---|---|---|
| 1. Origin: | human | | | |
| Age: | weaned | Sex: | F | |
| Type of delivery: | natural | Type of nutrition: | breast-fed | |
| 2. Genus | Lactobacillus | | | |
| 3. Morphology | Bacilli: | short | | |
| | chains | yes | | |
| | aggregates | no | | |
| | presence of a capsule | no | | |
| 4. Carbohydrate fermentation | | | | |

| | | | | | |
|---|---|---|---|---|---|
| Glycerol | − | Erythrol | − | D-Arabinose | − |
| L-Arabinose | − | D-Xylose | − | L-Xylose | − |
| Adonitol | + | β-methyl- | − | Galactose | + |
| D-Glucose | + | xyloside | | D-Mannose | + |
| L-Sorbose | + | D-Fructose | + | Esculin | + |
| Salicin | + | Rhamnose | − | Maltose | + |
| Lactose | + | Cellobiose | + | Sucrose | + |
| Trealose | + | Melibiose | − | Melezitose | + |
| D-Raffinose | − | Inulin | + | Glycogen | − |
| Xylitol | − | Starch | − | Dulcitol | − |
| Inositol | − | β-Gentiobiose | + | Sorbitol | − |
| Amygdalin | − | Mannitol | + | D-Turanose | + |
| D-Lyxose | − | Arbutin | + | D-Fucose | − |
| D-Arabitol | − | D-Tagatose | + | Gluconate | + |
| α-methyl-D-mannoside | − | L-Arabitol α-methyl-D-glucoside | − | | |
| N-acetyl-glucosamine | + | 2-keto-gluconate | − | | |
| 5-keto-gluconate | − | L-fucose | − | | |
| Ribose | + | | | | |
| 5. Plasmids: | two | | | | |

Chart 4 - Strain identification: CNCM I-1447

| | | | | |
|---|---|---|---|---|
| 1. Origin: | human | | | |
| Age: | newborn | Sex: | M | |
| Type of delivery: | natural | Type of nutrition: | breast-fed | |
| 2. Genus Species | Lactobacillus acidophilus | | | |
| 3. Morphology | Bacilli: | short | | |
| | chains | yes | | |
| | aggregates | no | | |
| | presence of a capsule | no | | |
| 4. Production of lactic acid | L D | 3.53 g/L 3.12 g/L | | |
| 5. Carbohydrate fermentation | | | | |

| | | | | | |
|---|---|---|---|---|---|
| Glycerol | − | Erythrol | − | D-Arabinose | − |
| L-Arabinose | − | D-Xylose | − | L-Xylose | − |
| Adonitol | − | β-methyl- | − | Galactose | + |
| D-Glucose | + | xyloside | | D-Mannose | + |
| L-Sorbose | − | D-Fructose | + | Esculin | + |
| Salicin | + | Rhamnose | − | Maltose | + |
| Lactose | − | Cellobiose | + | Sucrose | + |
| Trealose | + | Melibiose | − | Melezitose | + |
| D-Raffinose | − | Inulin | + | Glycogen | − |
| Xylitol | − | Starch | + | Dulcitol | − |
| Inositol | − | β-Gentiobiose | + | Sorbitol | + |
| Amygdalin | + | Mannitol | + | D-Turanose | + |
| D-Lyxose | − | Arbutin | + | D-Fucose | − |
| D-Arabitol | − | D-Tagatose | + | Gluconate | + |
| α-methyl-D-mannoside | − | L-Arabitol α-methyl-D-glucoside | − | | |
| N-acetyl-glucosamine | + | 2-keto-gluconate | − | | |
| 5-keto-gluconate | − | L-fucose | − | | |
| Ribose | − | | | | |
| 6. Plasmids: | one | | | | |

EXAMPLE 2

The strains of the present invention were compared with reference strains in order to evaluate the persistence of their ability to adhere to various types of cells, to grow at various pH values, to grow at various concentrations of bile and to grow under various incubation conditions, the ability to influence the growth of intestinal pathogens. Before each assay, lyophilized sample of the strains were rehydrated and incubated in MRS medium.

The reference strains were the following:

*Lactobacillus acidophilus* ATCC 53103

*Lactobacillus acidophilus* ATCC 4357

*Lactobacillus delbrueckii* ATCC 7994

*Salmonella enteritidis* IMM2

*Escherichia coli* ATCC 35401

Adhesion to Human Epithelial Cells

The adhesion tests were carried out "in vitro" on two types of epithelial cells:

freshly isolated human buccal cells, intestinal cells (collection cell line, Intestine 407, obtained from Instituto Zooprofilattico Sperimentale in Brescia).

The buccal cells were isolated from healthy non-smoking subjects. Cells were collected by scraping the internal surface of the cheeks with a wooden tongue. depressor. The cells of the oral mucosa were then washed with a PBS (Phosphate Buffered Saline) solution.

Intestinal cells were made to grow in Eagle's Basal medium in Hanks BSS, containing 10% of bovine foetal serum, and incubated at 37° C. under an atmosphere of 5% $CO_2$ for 48 h. The monostrata formed were trypsinized according to standard methods (elimination of the growth medium, washing of the substrate with PBS solution, addition of 2 mL of trypsin-versene at 0.25% concentration). The suspension obtained was then centrifuged at 1700 g for 10 min. The cells were washed twice with PBS solution and then diluted with the same solution until a concentration of 100 cells/mL was obtained.

The adhesion test was carried out by adding $10^7$ bacteria that had grown under suited conditions to $10^5$ epithelial cells (buccal or intestinal) in PBS solution. The mixture was incubated for 30 min at 37° C. and under continuous agitation. After that, the non-adhering bacteria were eliminated by filtering the suspension through a 5 μm diameter pores polycarbonate membrane (Sartorius). After repeated washing, the membranes were placed on a glass slide, dried in air, fixed with methanol and stained with crystal-violet in order to detect the adhering bacteria. The average number of bacteria that adhered per cell (X) was determined by counting the number of bacteria that adhered to 100 cells.

The adhesion of the strains under examination was compared to that of ATCC 53103 strain, taken as a reference, with the following equation:

$$\text{Adhesion Index } (A.I.) = \frac{n. \text{ of bacteria/epithelial cell}}{n. \text{ of ATCC 53103 lacto-bacilli/epithelial cell}} \times 100$$

The results of these experiments are reported in Table 1.

TABLE 1

Adhesion of the lactobacilli strains to buccal and human intestinal cells

| Strain | Buccal cells | | Intestinal cells | |
|---|---|---|---|---|
| | X ± SD | A.I. | X ± SD | A.I. |
| CNCM I-1390 | 27.3 ± 7.5 | 63.5 | 20.9 ± 6.1 | 123.7 |
| CNCM I-1391 | 49.1 ± 6.4 | 114.2 | 42.6 ± 5.9 | 252.1 |
| CNCM I-1447 | — | — | 14.4 ± 5.8 | 85.2 |
| ATCC 53103 | 43 ± 5.95 | 100.0 | 16.9 ± 5.3 | 100.0 |
| ATCC 4357 | 4 ± 3.2 | 9.3 | 2.9 ± 1.6 | 17.1 |
| ATCC 7994 | 3.1 ± 1.7 | 7.2 | 1.6 ± 1.5 | 9.5 |

X = number of lactobacilli per cell; SD = standard deviation; A.I. = adhesion index The results show the excellent ability of the strains of the present invention to adhere to the cells of the intestinal and buccal mucosa; in some cases it resulted far greater than the reference strains.

Growth at Various pH Values

The lactobacilli were grown in MRS (Oxoid) liquid medium at pH 3 (obtained by adding HCl), pH 5 (normal pH value of the medium) and pH 8 (obtained by adding NaOH).

The samples were incubated at 37° C. under a 5% $CO_2$ atmosphere, and bacterial cell were counted at various time intervals (12 h, 24 h, 48 h). The results of these experiments are illustrated in Table 2.

TABLE 2

Growth of the bacterial strains at various times and at various pH values

| Strain | pH3 | | | pH5 | | | pH8 | | |
|---|---|---|---|---|---|---|---|---|---|
| | 12 h | 24 h | 48 h | 12 h | 24 h | 48 h | 12 h | 24 h | 48 h |
| CNCM I-1390 | 5.0 | 6.8 | 6.5 | 9.6 | 10.0 | 10.3 | 9.5 | 9.7 | 9.5 |
| CNCM I-1391 | 4.9 | 6.5 | 6.3 | 9.5 | 9.8 | 10.6 | 9.5 | 9.5 | 10.4 |
| CNCM I-1447 | 4.5 | 4.8 | 4.0 | 9.0 | 9.8 | 9.6 | 9.0 | 9.4 | 9.3 |
| ATCC 53103 | 5.3 | 6.6 | 6.1 | 9.5 | 9.5 | 9.5 | 9.3 | 9.5 | 9.8 |
| ATCC 4357 | 4.0 | 4.6 | 4.8 | 7.5 | 8.6 | 8.8 | 7.8 | 8.0 | 8.5 |
| ATCC 7994 | <3 | <3 | <3 | 7.5 | 8.0 | 8.8 | <3 | <3 | <3 |

Values are expressed as log CFU/mL. CFU=Colony Forming Unit.

The results show that the strains of the present invention can grow under a wide range of pH values. In particular, the strains show a resistance to acidic pH values equal or superior to the reference strains.

Resistance to the Bile

The strains of the present invention and the reference strain ATCC 53103, were incubated for 48 h in MRS liquid medium. The broth cultures were diluted ($10^7$ CFU/mL) and grown on MRS agar supplemented with 1.5 g/L or 3 g/L of bile (Ox gall powder, Sigma). After 48 h of incubation at 37° C. under anaerobic conditions, the bacterial count was carried out in order to verify the resistance to the bile.

The results are illustrated in Table 3.

TABLE 3

Resistance of the lactobacilli strains to the bile

| Strain | MRS agar (control) CFU/mL | MRS + bile 1.5 g/L CFU/mL | MRS + bile 3.0 g/L CFU/mL |
|---|---|---|---|
| CNCM I-1390 | 140 | 134 | 90 |
| CNCM I-1391 | 187 | 186 | 176 |
| CNCM I-1447 | 289 | 283 | 290 |
| ATCC 53103 | 201 | 202 | 161 |

CFU = Colony Forming Unit.

The results show that the new strains have a good resistance to the bile, even at a high concentration. Particularly surprising was the resistance of the CNCM I-1447 even to the higher bile concentration value.

Growth Under Anaerobic and Aerobic Conditions

The lactobacilli were incubated overnight in MRS liquid medium at 37° C. under anaerobic and aerobic conditions and then counted. The results are indicated in Table 4.

TABLE 4

Growth of the lactobacilli under anaerobic and aerobic conditions

| Strain | Anaerobiosis log CFU/mL | Aerobiosis log CFU/mL |
|---|---|---|
| CNCM I-1390 | 9.6 | 9.1 |
| CNCM I-1391 | 10.0 | 10.1 |
| CNCM I-1447 | 9.8 | 9.7 |
| ATCC 4357 | 7.3 | 7.0 |
| ATCC 7994 | 9.3 | 9.9 |
| ATCC 53103 | 9.7 | 9.8 |

CFU = Colony Forming Unit.

The results show that the strains of the present invention grow both under anaerobic and aerobic conditions.

Interference on the Growth of Intestinal Pathogens

The ability of the strains of the pre sent invention to inhibit the growth of intestinal pathogens was evaluated in co-culture experiments with *Escherichia coli* (enterotoxigenic ATCC 35401) and *Salmonella enteritidis* (IMM2).

In a first series of experiments, the strains of the present invention and the reference strains were grown overnight, then they were inoculated with the pathogens at 37° C. under an atmosphere of 5% $CO_2$, in a culture medium consisting of a 1:1 mixture of MRS liquid medium at a double concentration and Mueller-Hilton liquid medium at a double concentration. After 24 h and 48 h, the bacterial counts of the pathogens and of the Lactobacillus strains under examination were carried out. Controls consisted in the pathogen and the Lactobacillus strains grown as a pure culture. The results of these experiments are reported in Tables 5 and 6.

In another series of experiments, the strains of the present invention and the reference strains were inoculated simultaneously with the pathogens, and grown together under the above indicated conditions. After 24 h and 48 h of incubation, the bacterial counts of the pathogens and of the Lactobacillus strains were carried out. Controls were as above described. The results of these experiments are reported in Tables 7 and 8.

The results of the experiments of the growth of the pathogens in co-culture with lactobacilli surprisingly show that the strains of the present invention are effective in inhibiting the growth of harmful microorganisms. In fact, as illustrated in Tables 5 and 6, the growth of *Escherichia coli* and of *Salmonella enteritidis* was strongly inhibited when a sufficient amount of lactobacilli was inoculated with these two pathogens (a value <3, expressed as log CFU/mL, was found in all the cases). The strains can inhibit the growth of the pathogens even when they are: inoculated simultaneously (Tables 7 and 8). In particular, in the case of *Salmonella enteritidis*, the same inhibition was observed when the lactobacilli were grown overnight and then inoculated (compare Table 8 and Table 6). Besides, it is interesting to note that the growth of the Lactobacillus strains is not influenced by the simultaneous presence of the pathogen. In all the experiments the data regarding the growth of the lactobacilli in the co-culture were comparable with those of the growth of the lactobacilli in the pure culture.

TABLE 5

Growth of the enterotoxigenic *Escherichia coli* (ATCC 35401) and lactobacilli in co-culture[1]

| | Bacterial growth (log CFU/mL) | | | |
|---|---|---|---|---|
| | *Escherichia coli* (ATCC 35401) | | Lactobacillus (examined strain) | |
| Culture | 24 h | 48 h | 24 h | 48 h |
| CNCM I-1390 | — | — | 9.9 | 10.8 |
| ATCC 35401 | 9.5 | 9.6 | — | — |
| CNCM I-1390 + ATCC 35401 | <3 | <3 | 9.8 | 10.6 |
| CNCM I-1391 | — | — | 9.5 | 10.8 |
| ATCC 35401 | 9.5 | 9.6 | — | — |
| CNCM I-1391 + ATCC 35401 | <3 | <3 | 9.8 | 10.9 |
| CNCM I-1447 | — | — | 9.6 | 9.9 |
| ATCC 35401 | 9.5 | 9.6 | — | — |
| CNCM I-1447 + ATCC 35401 | <3 | <3 | 9.6 | 9.8 |
| ATCC 53103 | — | — | 9.7 | 10.8 |
| ATCC 35401 | 9.5 | 9.6 | — | — |
| ATCC 53103 + ATCC 35401 | <3 | <3 | 9.8 | 10.9 |
| ATCC 4357 | — | — | 9.0 | 9.3 |
| ATCC 35401 | 9.5 | 9.6 | — | — |
| ATCC 4357 + ATCC 35401 | <3 | <3 | 9.0 | 9.6 |
| ATCC 7994 | — | — | 8.0 | 8.8 |
| ATCC 35401 | 9.5 | 9.6 | — | — |
| ATCC 7994 + ATCC 35401 | <3 | <3 | 8.6 | 8.8 |

[1]The lactobacilli were grown overnight and then inoculated with *Escherichia coli*. After 24 h and 48 h the bacterial counts of the pathogen and of the lactobacilli were carried out. CFU = colony forming unit.

TABLE 6

Growth of *Salmonella enteritidis* (IMM 2) and lactobacilli in a co-culture[1]

| | Bacterial growth (log CFU/mL) | | | |
|---|---|---|---|---|
| | *Salmonella enteritidis* (IMM 2) | | Lactobacillus (examined strain) | |
| Culture | 24 h | 48 h | 24 h | 48 h |
| CNCM I-1390 | — | — | 9.8 | 10.3 |
| IMM 2 | 9.5 | 9.7 | — | — |
| CNCM I-1390 + IMM 2 | <3 | <3 | 9.3 | 10.9 |
| CNCM I-1391 | — | — | 9.8 | 10.3 |
| IMM 2 | 9.5 | 9.7 | — | — |
| CNCM I-1391 + IMM 2 | <3 | <3 | 9.9 | 10.9 |
| CNCM I-1447 | — | — | 9.5 | 9.8 |
| IMM 2 | 9.5 | 9.7 | — | — |
| CNCM I-1447 + IMM 2 | <3 | <3 | 9.3 | 9.9 |
| ATCC 53103 | — | — | 9.6 | 9.9 |
| IMM 2 | 9.5 | 9.7 | — | — |
| ATCC 53103 + IMM 2 | <3 | <3 | 9.7 | 10.9 |
| ATCC 4357 | — | — | 8.3 | 9.0 |
| IMM 2 | 9.5 | 9.7 | — | — |
| ATCC 4357 + IMM 2 | <3 | <3 | 8.6 | 8.8 |
| ATCC 7994 | — | — | 8.7 | 8.3 |
| IMM 2 | 9.5 | 9.7 | — | — |
| ATCC 7994 + IMM 2 | <3 | <3 | 8.7 | 8.3 |

[1]The lactobacilli were grown overnight and then inoculate with *Salmonella enteritidis*. After 24 h and 48 h the bacterial counts of the pathogen and of the lactobacilli were carried out. CFU = colony forming unit.

TABLE 7

Growth of enterotoxigenic *Escherichia coli* (ATCC 35401) and lactobacilli in a co-culture after simultaneous inoculation[1]

| | Bacterial growth (log CFU/mL) | | | |
|---|---|---|---|---|
| | *Escherichia coli* (ATCC 35401) | | Lactobacillus (examined strain) | |
| Culture | 24 h | 48 h | 24 h | 48 h |
| CNCM I-1390 | — | — | 10.3 | 11.0 |
| ATCC 35401 | 9.7 | 9.8 | — | — |
| CNCM I-1390 + ATCC 35401 | 5.5 | 4.6 | 9.8 | 11.4 |
| CNCM I-1391 | — | — | 10.0 | 10.9 |
| ATCC 35401 | 9.7 | 9.8 | — | — |
| CNCM I-1391 + ATCC 35401 | 5.3 | 5.2 | 9.7 | 11.4 |
| CNCM I-1447 | — | — | 9.6 | 9.8 |
| ATCC 35401 | 9.7 | 9.8 | — | — |
| CNCM I-1447 + ATCC 35401 | 5.6 | 5.0 | 9.6 | 9.8 |
| ATCC 53103 | — | — | 9.8 | 10.9 |
| ATCC 35401 | 9.7 | 9.8 | — | — |
| ATCC 53103 + ATCC 35401 | 4.9 | 5.0 | 9.5 | 11.0 |
| ATCC 4357 | — | — | 9.0 | 9.3 |
| ATCC 35401 | 9.7 | 9.8 | — | — |
| ATCC 4357 + ATCC 35401 | 5.6 | 5.3 | 8.9 | 9.5 |
| ATCC 7994 | — | — | 8.8 | 8.9 |
| ATCC 35401 | 9.7 | 9.8 | — | — |

TABLE 7-continued

Growth of enterotoxigenic *Escherichia coli* (ATCC 35401) and lactobacilli in a co-culture after simultaneous inoculation[1]

| | Bacterial growth (log CFU/mL) | | | |
|---|---|---|---|---|
| | *Escherichia coli* (ATCC 35401) | | *Lactobacillus* (examined strain) | |
| Culture | 24 h | 48 h | 24 h | 48 h |
| ATCC 7994 + ATCC 35401 | 5.4 | 5.0 | 8.6 | 8.9 |

[1]The lactobacilli and *Escherichia coli* were inoculated simultaneously, and after 24 h and 48 h the bacterial counts of the pathogen and of the lactobacilli were carried out. CFU = colony forming unit.

TABLE 8

Growth of *Salmonella enteritidis* (IMM 2) and lactobacilli in a co-culture after simultaneous inoculation[1]

| | Bacterial growth (log CFU/mL) | | | |
|---|---|---|---|---|
| | *Salmonella enteritidis* (IMM 2) | | *Lactobacillus* (examined strain) | |
| Culture | 24 h | 48 h | 24 h | 48 h |
| CNCM I-1390 | — | — | 9.6 | 10.7 |
| IMM 2 | 9.7 | 9.6 | — | — |
| CNCM I-1390 + IMM 2 | <3 | <3 | 9.1 | 11.7 |
| CNCM I-1391 | — | — | 9.6 | 10.7 |
| IMM 2 | 9.7 | 9.6 | — | — |
| CNCM I-1391 + IMM 2 | <3 | <3 | 10.0 | 10.5 |
| CNCM I-1447 | — | — | 9.5 | 9.8 |
| IMM 2 | 9.7 | 9.6 | — | — |
| CNCM I-1447 + IMM 2 | <3 | <3 | 9.2 | 9.7 |
| ATCC 53103 | — | — | 9.7 | 10.3 |
| IMM 2 | 9.7 | 9.6 | — | — |
| ATCC 53103 + IMM 2 | <3 | <3 | 9.1 | 11.5 |
| ATCC 4357 | — | — | 8.8 | 9.5 |
| IMM 2 | 9.7 | 9.6 | — | — |
| ATCC 4357 + IMM 2 | <3 | <3 | 9.0 | 9.3 |
| ATCC 7994 | — | — | 8.8 | 9.0 |
| IMM 2 | 9.7 | 9.6 | — | — |
| ATCC 7994 + IMM 2 | <3 | <3 | 8.0 | 8.5 |

[1]The lactobacilli and *Salmonella enteritidis* were inoculated simultaneously, and after 24 h and 48 h the bacterial counts of the pathogen and of the lactobacilli were carried out. CFU = colony forming unit.

In another series of experiments, mixtures of lactobacilli of the present invention were inoculated with *Escherichia coli* and *Salmonella enteritidis* in order to evaluate whether or not such mixtures could exert a synergistic effect in the inhibition of the growth of pathogenic strains. Table 9 reports some of the results obtained with the enterotoxigenic *Escherichia coli* strain ATCC 35401 in co-culture with the lactobacilli simultaneously inoculated.

TABLE 9

Inhibition of enterotoxigenic *Escherichia coli* (ATCC 35401) growth by various lactobacilli mixtures in co-culture after simultaneous inoculation[1]

| | Bacterial growth (log CFU/mL) *Escherichia coli* (ATCC 35401) | |
|---|---|---|
| Culture | 24 h | 48 h |
| ATCC 35401 | 8.65 | 8.72 |
| ATCC 35401 + CNCM I-1390 + CNCM I-1391 | 3.40 | <2 |
| ATCC 35401 + CNCM I-1390 + CNCM I-1447 | 3.18 | 2.70 |
| ATCC 35401 + CNCM I-1391 + CNCM I-1447 | <2 | <2 |
| ATCC 35401 + CNCM I-1390 + CNCM I-1391 + CNCM I-1447 | 2.30 | <2 |

[1]*Escherichia coli* was inoculated simultaneously with various mixtures of lactobacilli. After 24 h and 48 h, the bacterial counts of the pathogen and of the lactobacilli were carried out. CFU = colony forming unit.

The data clearly show that the lactobacilli mixtures were able to completely inhibit the growth of the pathogen after both 24 and 48 h. Moreover the lactobacilli mixtures were more effective in inhibiting the growth of the pathogen than the single Lactobacillus strain (compare Table 9 with Table 7). These data were obtained with the pathogen inoculated simultaneously with the lactobacilli. Also in these experiments, the growth of the lactobacilli was unaffected by the simultaneous presence of the pathogen and of other lactobacilli strains as well. Similar results were obtained with *Salmonella enteritidis*.

From the above reported results, it is evident that the strains of the present invention are endowed with a series of features that make them particularly suited for the preparation of drugs. The strains of the present invention have the ability to adhere to the human epithelial cells (an important characteristic for colonization), and they have a good when not excellent resistance to bile. They can resist and grow at acidic pH values, and can grow under both anaerobic and aerobic conditions. Furthermore, the strains of the present invention taken alone or in a mixture thereof show a surprising ability to inhibit the growth of pathogens in the gastrointestinal tract. These properties are maintained after lyophilization.

The resistances of the strains of the present invention to lyophilization vary from 35 to 60% after 3 months at 4° C. They also present a high speed of growth and absence of lysogeny.

These characteristics make the strains particularly suited for the prophylaxis and treatment of disease caused by contaminated food or water and as adjuvants during treatment with antibiotics or under general stress conditions. Besides, their stability makes their possible use in the prophylaxis and treatment of pathologies affecting the frequent travellers particularly promising. The strains are also particularly suited for treating newborns in all those situations in which intestinal colonization by less favourable microorganisms may occur (e.g., caesarian born babies, premature babies, bottle-fed babies). Finally they can also be employed in the manufacture of milk and related food products.

The following new human Lactobacillus non-acidophilus strains under accession numbers CNCM I-1390, CNCM I-1391 and CNCM I-1392 and the following new human *lactobacillus acidophilus* strain under accession number CNCM I-1447 were deposited under the terms of the Budapest Treaty on Jul. 13, 1994 at the Collection Nationalee de Cultures de Microorganismes, Institut Pasteur, 28 Rue de Docteur Roux, F-75724, Paris CEDEX 15.

REFERENCES

1. Drasar B. S., Hill M. J. (1974) Human intestinal flora, Academic Press, London.
2. Bottazzi V. et al. (1981) Probiotica con batteri lattici, Centro Sperimentale Latte, Milano.
3. Gilliland S. E. et al. (1978) Influence of consuming non fermented milk containing Lactobacillus acidophilus on fecal flora of healthy males. J. Dairy Sci. 61, 1–10.
4. Flora intestinale normale nel bambino e sue modificazioni in condizioni patologiche, Analisi Istituto Superiore di Sanità, Roma, 1986.
5. Bottazzi V. (1987) Aggiornamenti di Microbiologia dei batteri lattici, Centro Sperimentale Latte, Milano.
6. Aly R., Shinefield H. R. (1982) Bacterial Interference, CRC Press, Boca Raton, U.S.A.
7. Shapiro S. (1960) Control of antibiotic-induced gastrointestinal symptoms with yogurt. Clinical Medicine, 295–299.
8. Gumma A. et al. (1972) Etude de quelque procédés galéniques appliqués à la thérapeutique de substitution par Lactobacillus acidophilus. Pharm. Acta Helv. 47, 433–437.
9. Gilliland S. E. (1979) Beneficial interrelationships between certain microorganisms and humans: candidate microorganisms for use as dietary adjuncts. J. Food Protect. 42, 164–167.
10. Lee A. (1985) Neglected niches: the microbial ecology of the gastrointestinal tract. Advances in Microbial Ecology 8, 115–162, Marshall K. C.— Plenum Press N.Y.
11. Zoppi G. et al. (1982) Oral bacteriotherapy in clinical practice. Eur. J. Pediatr. 139, 18–21.
12. Akiyoshi H. et al. (1977) Isolation and characterization of an inhibitory substance against Escherichia coli produced by Lactobacillus acidophilus. Milchwissenschaft 32, 727–730.
13. Babel F. J. (1977) Antibiosis by lactic culture bacteria J. Dairy Sci. 60, 815–821.
14. Barefoot S. F., Klaenhammer T. R. (1983) Detection and activity of Lactacin B., a bacteriocin produced by Lactobacillus acidophilus. Appl. Environ. Microbiol. 45, 1808–1815.
15. Tagg J. R. et al. (1976) Bacteriocins of gram positive bacteria. Bacteriol. Rev. 40, 722–756.
16. Silva M. et al. (1987) Antimicrobial substance from a human Lactobacillus strain. Antimicrob. Agents Chemother. 31, 1231–1233.
17. Fuller R., Brooker B. E. (1980) The attachment of bacteria to the squamous epithelial cells and its importance in the microecology of the intestine, in Microbial adhesion to surfaces (Berkeley R. C. W., Lynch J. M., Melling J., Rutter P. R., Vincent B., Eds.), Society of Chemical Industry/Ellis Horwood Ltd, London.
18. Bottazzi V. et al. (1985) Proprietà antitumorali dei batteri lattici e degli alimenti fermentati con batteri lattici. Il Latte 10, 873–879.
19. Van Der Waaij D. (1979) The colonization resistance of the digestive tract in experimental animals and its consequences for infection prevention, in New Criteria for Antimicrobial Therapy (Excerpta Medica, Ed.), Utrecht.
20. Savage D. C. (1977) Microbial ecology of the gastrointestinal tract. Annu. Rev. Microbiol. 31, 107–133.
21. Ray B., Johnson M. C. (1986) Freeze-drying injury of surface layer protein and its protection in Lactobacillus acidophilus. Cryo-Lett. 7, 210.
22. Sharpe M. E. (1981) The genus Lactobacillus, in: The Prokaryotes (Starr, Stolp, Truper, Balows, Schlegel, Ed.), pp 1653–1679, Springer, N.Y.
23. Morelli L. et al. (1982) Characterization of plasmid DNA molecules in L. acidophilus strain D137. Annali di Microbiologia 32, 99–105.
24. Davies F. L. et al. (1982) The value of plasmid profiles for strain identification in lactic streptococci and the relationship between Streptococcus lactis 712, ML2 and C2. J. Appl. Bacteriol. 51, 325–337.
25. Kersters K., De Ley J. (1980) Classification and identification of bacteria by electrophoresis of their proteins, in Microbiological classification and identification (Goodfellow M.&Board R. G., Ed.), pp 273–297, Academic Press, London.
26. Vescovo M. et al. (1982) Drug resistance plasmids in Lactobacillus acidophilus and Lactobacillus reuteri. Appl. Environ. Microbiol. 43, 50–56.
27. Reniero et al. (1991) Detection of permanent Lactobacillus casei subsp. casei strains in weaned infants 'gut'. Lett. Appl. Microbiol. 13, 3–6.

We claim:

1. Isolated Lactobacillus genus strains, deposited at the CNCM collection of the Institut Pasteur, under accession numbers I-1390, I-1391, I-1392 or I-1447.

2. A pharmaceutical, veterinary or alimentary composition comprising at least one of isolated Lactobacillus acidophilus or non-acidophilus strains selected from the group consisting of deposits CNCM I-1390, CNCM I-1391, CNCM I-1392 and CNCM I-1447 in a mixture with a carrier.

3. The composition according to claim 2, comprising a mixture of two or more of said strains in which at least one of the strains belongs to the Lactobacillus acidophilus species, and at least one belongs to a non-acidophilus species.

4. The composition according to claim 2 containing a mixture of all the strains CNCM I-1390, CNCM I-1391, CNCM I-1392 and CNCM I-1447.

5. The composition according to claim 2, wherein said isolated Lactobacillus strain is present in lyophilized form.

6. The composition according to claim 2 in the form of capsules, solutions or drinkable suspensions or powder in sachets.

7. The composition according to claim 2 containing from $10^6$ to $10^{10}$ cells of each strain per single dose.

* * * * *